United States Patent [19]

Nymark et al.

[11] Patent Number: 5,147,372
[45] Date of Patent: Sep. 15, 1992

[54] BIOPSY ARC MEANS AND THE USE OF THE SAME

[76] Inventors: Bernt Nymark, S-931 45; Gunnar Näsström, S-931 51, both of Skellefteå, Sweden

[21] Appl. No.: 634,884
[22] PCT Filed: Jul. 13, 1989
[86] PCT No.: PCT/SE89/00411
 § 371 Date: Jan. 11, 1991
 § 102(e) Date: Jan. 11, 1991
[87] PCT Pub. No.: WO90/00372
 PCT Pub. Date: Jan. 25, 1990

[30] Foreign Application Priority Data

Jul. 13, 1988 [SE] Sweden ................. 8802620

[51] Int. Cl.⁵ .............................. A61B 19/00
[52] U.S. Cl. ................. 606/130; 378/197; 604/116
[58] Field of Search ............ 378/4, 9, 13, 19–21, 378/197; 604/116; 606/56, 96, 98, 102, 104, 171, 212, 130; 128/633, 660.06–660.09, 754

[56] References Cited

U.S. PATENT DOCUMENTS

| | | | |
|---|---|---|---|
| 4,115,696 | 9/1978 | Truscott | 378/197 |
| 4,350,159 | 9/1982 | Gouda | 606/130 |
| 4,360,028 | 11/1982 | Barbier et al. | 606/212 |
| 4,463,758 | 8/1984 | Patil et al. | |
| 4,608,977 | 9/1986 | Brown et al. | 606/130 |
| 4,638,798 | 1/1987 | Shelden et al. | 606/130 |
| 4,672,957 | 6/1987 | Hourahane | 606/96 |

FOREIGN PATENT DOCUMENTS

| | | | |
|---|---|---|---|
| 3339259 | 3/1985 | Fed. Rep. of Germany | 606/130 |
| 0740241 | 6/1980 | U.S.S.R. | 606/56 |
| 1149952 | 4/1985 | U.S.S.R. | 606/56 |
| 0907977 | 10/1962 | United Kingdom | 128/303 B |

*Primary Examiner*—Stephen C. Pellegrino
*Assistant Examiner*—Glenn K. Dawson
*Attorney, Agent, or Firm*—Burns, Doane, Swecker & Mathis

[57] ABSTRACT

The invention relates to a biopsy arc intended to be the support of examination needles in connection with computer tomography. The arc is removably secured to the patient's table and angularly adjustable to be adapted to the direction of the respective section image plane. The arc has a plurality of apertures directed towards the area enclosed by the arc for guiding the examination needles. The arc is made of a material which has an attenuation with respect to X-ray radiation which lies at or below the value exhibited by organic tissue, whereby the arc as well as organs can be brought to appear and stand out together on the section picture in order that a suitable aperture and direction of examination can be selected without risk of disturbing artefacts.

22 Claims, 4 Drawing Sheets

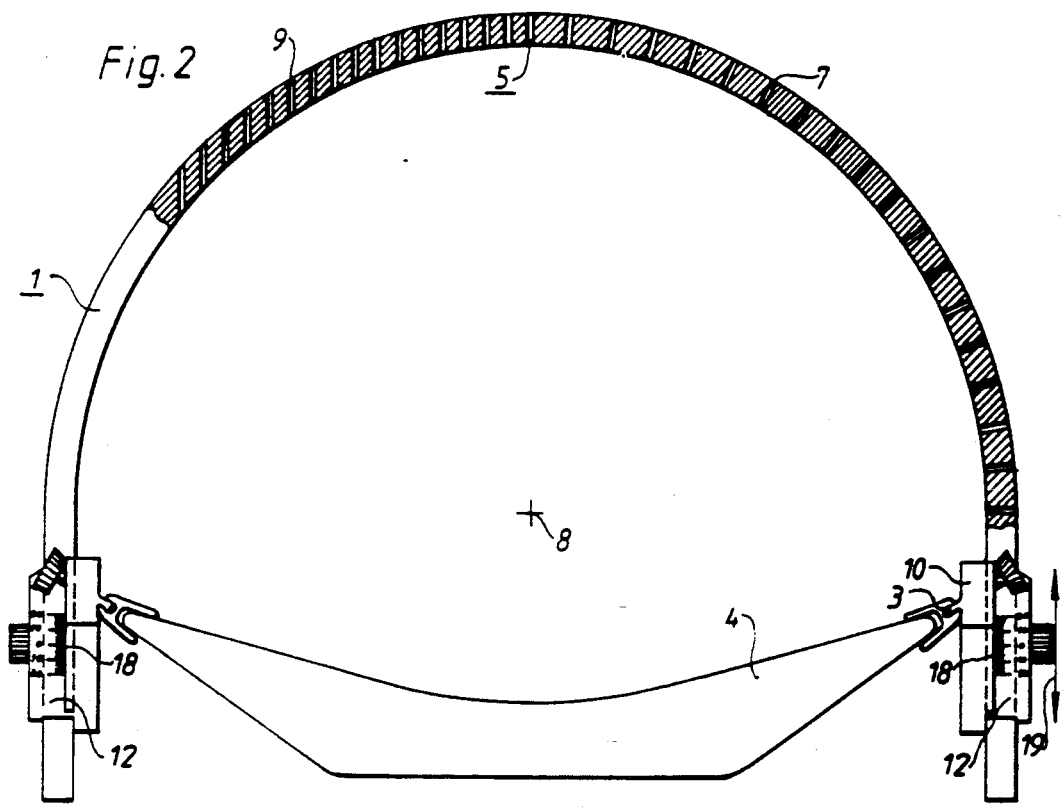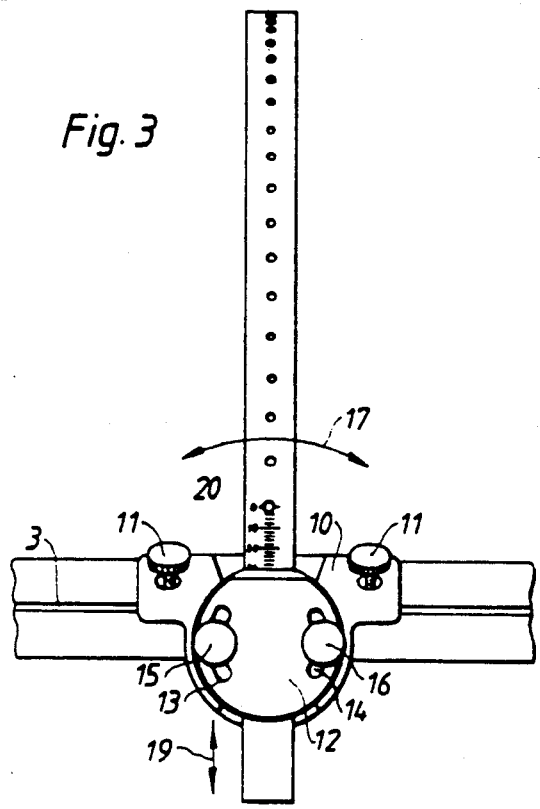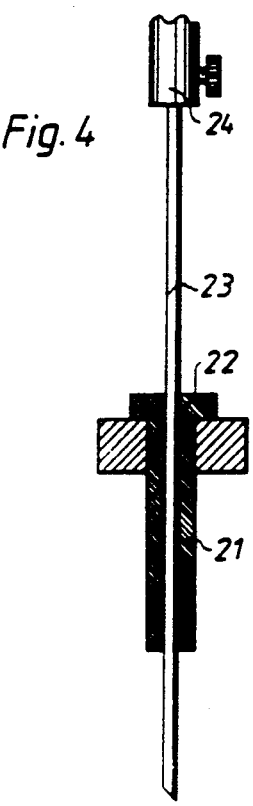

BIOPSY ARC MEANS AND THE USE OF THE SAME

TECHNICAL FIELD

In connection with computed tomographic examinations nowadays often so called biopsy arcs are used, that is, guiding instruments for inserting properly and safely examination means, such as sampling needles and the like, into the patient body concerned. Usually such biopsy arcs are provided with complicated adjustment means for directing the needles, and they require that the operating personnel be thoroughly trained in order that said means be used in an appropriate manner. Furthermore there are very often a risk of so called disturbing artefacts caused by the structure of the devices when these come into the vicinity of the section image. In examinations of the said kind it is thus very important that the occurring section images of the patient body concerned are not disturbed by structural material attenuating the radiation, as the contents of the images can easily be misinterpreted in such cases.

PRIOR ART

In this technical field there are a plurality of known designs, as can be seen from the patent literature. As an example the German Publication DE 32 05 915 can be mentioned. The device shown in this paper includes an arc which encloses substantially 270° of a circle and is secured to a patient's table. On the arc, which is provided with indicia, there is a slider to be slidably pushed along the arc. The slider includes a needle carrier which is movable about an axis and thus able to be turned in the plane of the arc. After a section image of a body under examination has been studied and the organ to be examined or punctured has been localized, the approximate insert angle of the needle is determined, also the depth of insertion, after which the needle carrier is set on the arc in the estimated position and approximately directed. Then the needle is inserted into the patient and loosened from the arc in order that a check picture be taken and the needle position obtained evaluated. Should positioning not be carried out exactly as intended the needle has to be pulled out, a new directing operation be carried out and the needle be inserted again. This is of course not satisfactory neither with respect to the examination nor to the patient.

The German Patent Specification DE 33 39 259 discloses an arc arrangement provided with some radial apertures through which guide means can be inserted for, in this case, drilling. The arrangement has no direct bearing on computed tomography but still it is mentioned as representing prior art guiding instruments.

As an example of usually occurring biopsy arc arrangements reference is made to the U.S. Pat. Nos. 4,350,159 and 4,463,758. These arrangements both include advanced structures for adjusting needles when carrying out examinations of the said type in connection with computed tomography. As can be clearly seen from the structure of these arrangements very disturbing artefacts can arise in the tomographic pictures if parts of the structures concerned should enter into the respective section picture.

Thus there is a need of a simple and safe method of determining the position as well as the penetration depth of an examination needle without it being necessary to resort to either intricate trigonometric calculations or complicated apparatus adjustments.

SUMMARY OF THE INVENTION

The present invention solves the problem mentioned above in a very simple and appropriate manner. A biopsy arc according to the invention, in particular for computed tomography, is provided with a plurality of apertures directed towards the area within the arc, the arc being mounted in such a way that it can be angularly set for adjustment of the plane of the arc to a plane of image section in the computed tomographic apparatus. Furthermore, the arc should be such as to exhibit such an attenuation of the radiation concerned which is equal to or less than that exhibited by organic issue. The arc will then form part of the related section image, whereby the directions of the apertures will be identifiable. Hereby it is possible, in order to select to suitable path for inserting an examination means, to select a suitably directed aperture through which said means can be inserted. Expediently the apertures have such a diameter that they can receive guiding sleeves for the examination means concerned, such as a needle or the like. Thanks to the fact that the arc has apertures of a comparatively large size these apertures will be clearly depicted in the section image as channels of given directions. Hence, it is comparatively simple to select an aperture for inserting an examination means if, in the image, the direction of the aperture agrees with the desired path of insertion. Contrary to what is occurring in known techniques the biopsy arc is allowed to remain in the path of the X-ray beam creating the image section, in order to render it possible to utilize the arc configuration in the section image in connection with the examination contemplated.

The characterizing features of the present invention appear from the patent claims following the specification.

The invention will be described in greater detail with reference to the accompanying drawings which illustrate embodiments of the invention.

IN THE DRAWINGS

FIG. 2 shows said arc partly in section.

FIG. 3 shows a lateral view of the arc.

FIG. 4 shows a guiding sleeve and an examination needle inserted in the same.

DISCLOSURE OF EMBODIMENTS

Figure 1:
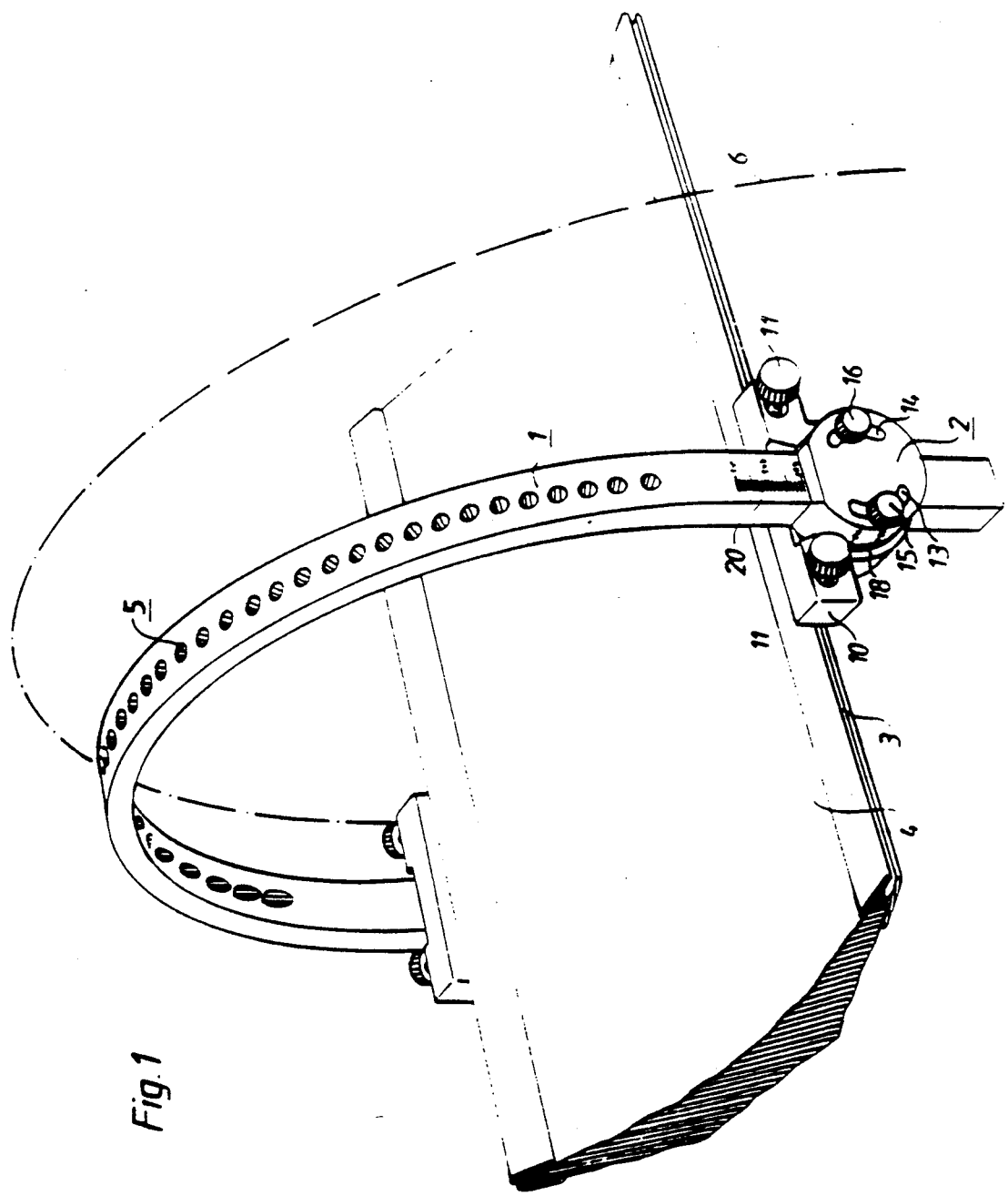
FIG. 1 shows a biopsy arc in accordance with the invention in perspective and mounted on a patient base.

The biopsy arc 1 shown in FIG. 1 is connected, by a detachable support member 2, with guide rails 3 or either side of a patient's table 4. The biopsy arc is provided with a plurality of apertures 5. Patient's table 4 is insertable in a computed tomography installation 6, in a manner not to be described in detail.

As seen from FIG. 2 there are, on one half of the biopsy arc, a number of radially extending apertures 7 which are directed towards a central target point 8. On the opposite side of the arc 1 there are a number of apertures 9 parallel with each other and chordally directed.

As can be clearly seen in FIGS. 2 and 3 the support member 2 of the biopsy arc 1 is provided with a slide 10 intended to run along the respective side rail 3 and to be locked to the rail in desired positions by means of set screws 11. The biopsy arc 1 itself can be clamped by its legs or shanks against the respective slide 10 by means of a plate 12 having slits 13, 14 through which retaining screws 15, 16 are inserted. By the slit arrangement 13, 14 the biopsy arc 1 can be adjusted in various angular positions in relation to the patient's table 4, as indicated by the double arrow 17. To this end indicia 18 are provided on the side of each plate 12. The disengageable clamping of the biopsy arc shanks by means of the plates 12 and the retaining screws 15, 16 brings with it that a certain adjustment of height can be performed in order to adjust to the body of the patient concerned, as indicated by the double arrow 19. On the biopsy arc 1 itself indicia 20 are provided on each shank.

To make it possible to guide and secure an examination needle in the desired position in any of the apertures 5 a sleeve 21 having a flange 22 is provided. The sleeve is made with a central through hole, through which a needle 23 can be inserted, as shown in FIG. 4. Suitable a socket 24 is pushed onto the needle, to be secured to the needle by a set screw. Hereby an insertion stop is provided, whose position is adjusted in accord with the required length to which the needle is to be inserted into the patient's body. The device shown in FIG. 4 has the advantage that only the needle 23 and the sleeve 21, 22 need be sterilized between various examinations of a patient, thus not the arc proper.

The biopsy arc 1 is made of a material having a density and properties in relationship to the X-ray radiation concerned which can be ranked in the same category as organic tissue density, that is, the density of tissue occurring in a patient's body. The density of tissue generally lies between 40 and 150 Hounsfield units, abbreviated H-units. To clarify the meaning of H-units the following may be pointed out. As it is not practical to work with $\mu$-values in computed tomographic scanning a new scale of values related to the linear attenuation coefficient have been defined by Hounsfield. The unit in this new scale is abbreviated H (meaning Hounsfield).

The scanning device used by Hounsfield operated at 120 kV with an aluminium filter of thickness 4.5 mm and a water container 27 cm thick. Under these particular conditions it was found that the $\mu$-value of water was 0.19 cm$^{-1}$ (i.e. 0.19 per cm), which is equivalent to the $\mu$-value of water measured by a monocromatic beam of 73 keV. In consequence herewith a Houndsfield unit for a substance 'x' is defined by the following equation $$H = 1000 \frac{\mu x - \mu\, H_2O\ (\text{at 73 keV})}{\mu\, H_2O\ (\text{at 73 keV})}$$

or $H = 5263\, \mu x - 1000$

It is important to know that the above equation is based on the prerequisite that 10 H-units correspond to a change of 1% of $\mu x$, in relation to the $\mu$-value of water.

From the above formula it can be calculated that H of water is 0 while the value of air is $-1000$ and that the value of dense bone tissue can raise up to $+3095$ H . A scanning system can thus handle 4096 different H-values for each image element. H-values of some anatomic substances and synthetic materials are shown in the table below.

| | |
|---|---|
| Dense bone tissue | up to 3095 |
| Bone | 200–1000 |
| Teflon | 950 |
| Delrin | 365 |
| Bakelite | 264 |
| Perspex | 125 |
| Lexan | 105 |
| Nylon | 89 |
| Dense tumour tissue | 50–90 |
| Coagulated blood | 55–75 |
| Brain tissue (grey) | 36–46 |
| Brain tissue (white) | 22–32 |
| Blood | 12 |
| Water | 0 |
| Polystyrene | $-28$ |
| Fat | $-100$ |
| Air | $-1000$ |

Thus the material density of the biopsy arc must not exceed such values that artefact disturbances can arise in the image concerned. Preferably the material should have a value below 200 H.

Polyamide plastics, having a H-value about 80, is satisfactory for most practical purposes. What is essential is the feature that the arc stands out in the section image so that the respective aperture and its direction can be identified.

USE AND FUNCTION OF THE ARRANGEMENT

Figure 5:
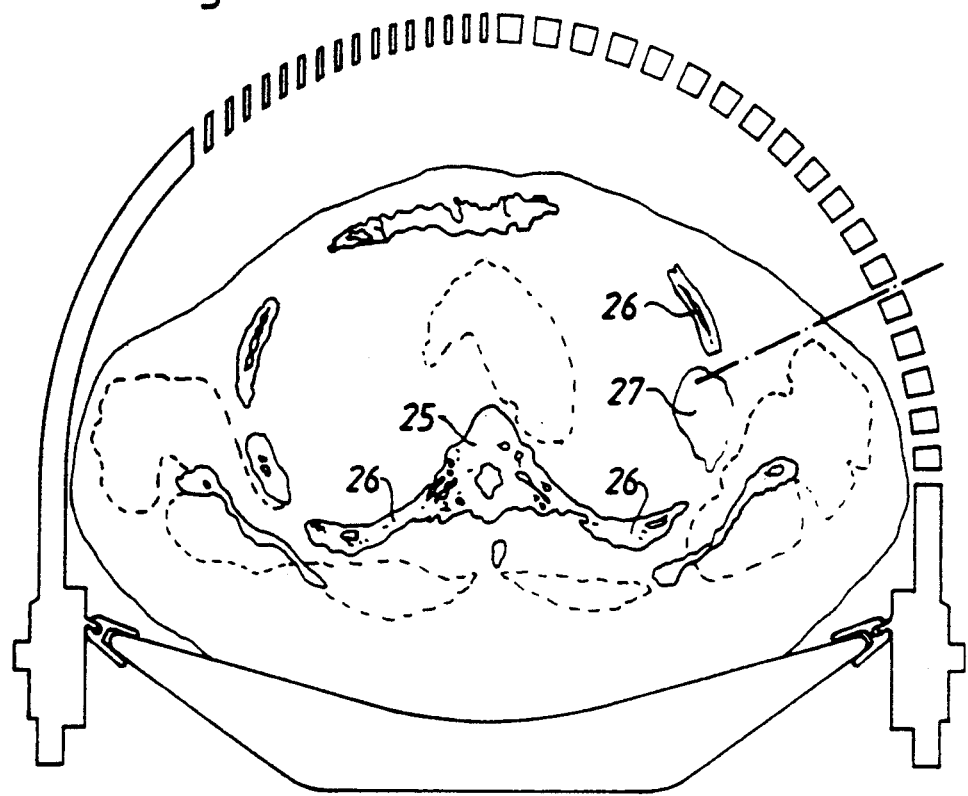
FIG. 5 shows a tomographic section picture with the biopsy arc outlined therein.

Examination of a patient while using the biopsy arc according to the invention is conducted in the following way:

In modern computed tomographic installations there are laser light beams for positioning so that the section plane of the scanning unit can be projected on the patient's body, after which pencil markings can be made. The biopsy arc is then secured to the patient's table 4 and angularly adjusted in accordance with the markings drawn so that the plane of the arc will coincide with the plane of the image section of the computed tomograph. When the patient's table 4 is again introduced into the tomograph 6 and the requested section pictures are taken, the arc with its apertured channels will be outline in each picture together with the organic tissues occurring in the image section, in a way as illustrated in FIG. 5. It is assumed that in FIG. 5 a vertebra 25 with ribs 26 belonging thereto are outlined in the picture. Within the area designated 27 the image of swollen organ stands out which, for example, is to be punctured. Now, the question is to insert the puncturing needle to this organ in such a way that no adjacent organs are damaged. So in this case one of the apertures 7 is selected which as to its direction seems to be the suitable one for reaching the said organ 27, as indicated by the dashed line.

Figure 6:
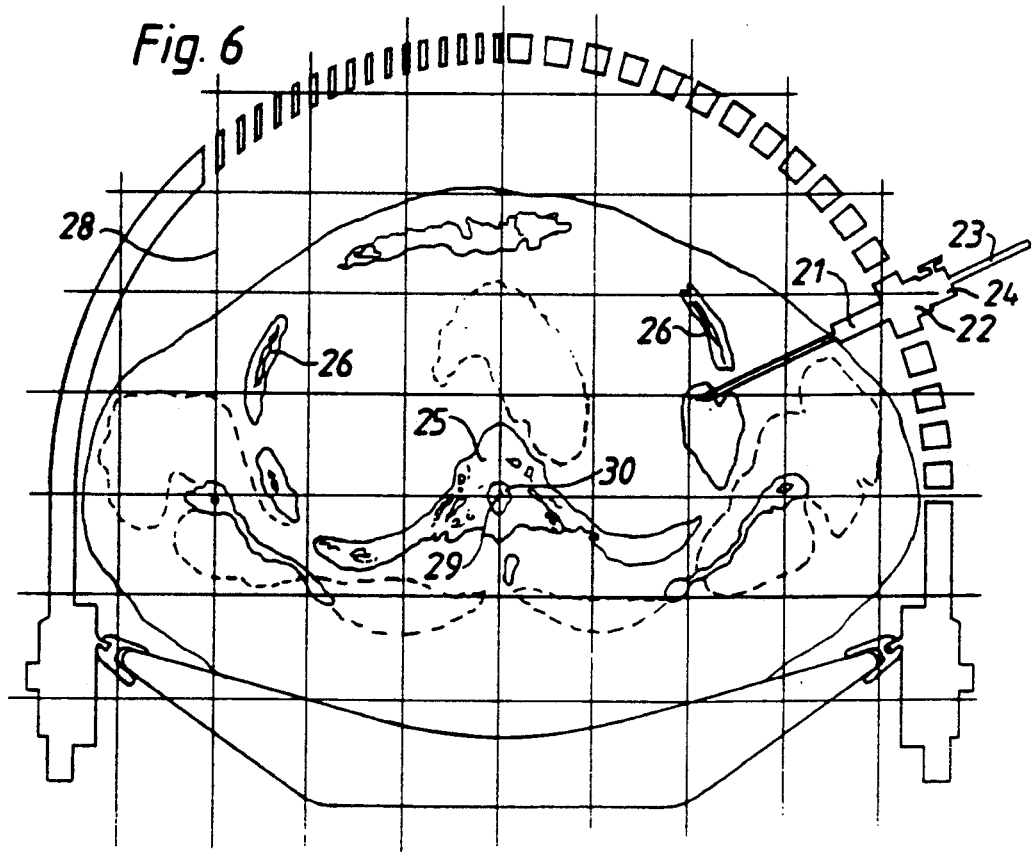
FIG. 6 shows essentially the same picture as FIG. 5 but with a computer designed reference grid applied.

However, in order to make it possible to determine the path and depth of needle penetration a reference grid 28 having a center line 29 is applied on the monitor image obtained, as seen in FIG. 6, said center line passing in this case through the spinal cord portion 30 of the vertebra 25. The reference grid is used to find the point 8 towards which the radially directed channels converge, in doing which there is marked on the center line 29, which coincides with the radial direction of the central aperture of the arc, the point which forms the target point of all radial apertures 7, that is, point 8 in FIG. 2. Starting from said point lines can then be drawn towards apertures 7 in order to select a suitable path of insertion and the associated needle. This reference grid is divided into such measuring units that they are directly, or by computer, convertable to the penetration depth of the puncturing needle concerned. In practice it is advisable to design the software of the computer such that measures of the depth of penetration and also of the needle socket length can be readily read by cursor control. As have been previously pointed out in connection with FIG. 4, the length of insertion is set by means of the socket 24 which abuts the flange 22 of the sleeve 21 when the proper length of the needle has been inserted.

Thus when the position of an organ 27 has been established a suitable aperture in the arc is selected in accordance with the above, i.e. an aperture having the correct direction towards the organ. The needle length is adjusted as described, after which the patient's table 4 with the patient is pulled out from the computed tomograph, and with the arc in its set position the aperture 7 concerned is used for inserting of the sleeve 21 and said needle 23. The needle is inserted to the depth aimed at and the patient can now be introduced again with the table 4 into the computed tomograph so that a picture for checking can be taken. It should be noted that it is not necessary to remove the arc when checking the position of the needle, as the arc, the needle, as well as the guide sleeve 21 can be allowed to appear in the section image, and this without any disturbing artefacts arising. The result of the organ puncture can also be checked in this manner with all settings unchanged.

If, in viewing the section image, it is seen that the radial apertures 7 cannot be used for the necessary measure, the biopsy arc can readily be turned by its shanks being pulled out from their engagement with the respective support member 2 and turned 180° so that the chordally directed apertures 9 are now located on the side where the organ 27 is situated. A suitable aperture having the requested position and direction can now be selected for the examination intended. In this case lines parallel with the line 29 of the reference grid 28 will now be essentially parallel with the direction of needle introduction, rendering it easy to read the depth of penetration. As can be seen the use of a biopsy arc according to the invention involves only a small number of manipulation steps and calculations as compared with known designs. Thanks to the feature that the arc can be allowed to form part of the examination image without creating disturbing obstacles and that it is possible to determine in a simple way from this image apertures and positions for inserting the needle, contribution is given to a perspicuity which is very valuable in the practical work involved in computed tomographic examinations. In view of its simple structure and the perspicuous way the arc is used its handling will be very easy to learn.

Figure 7:
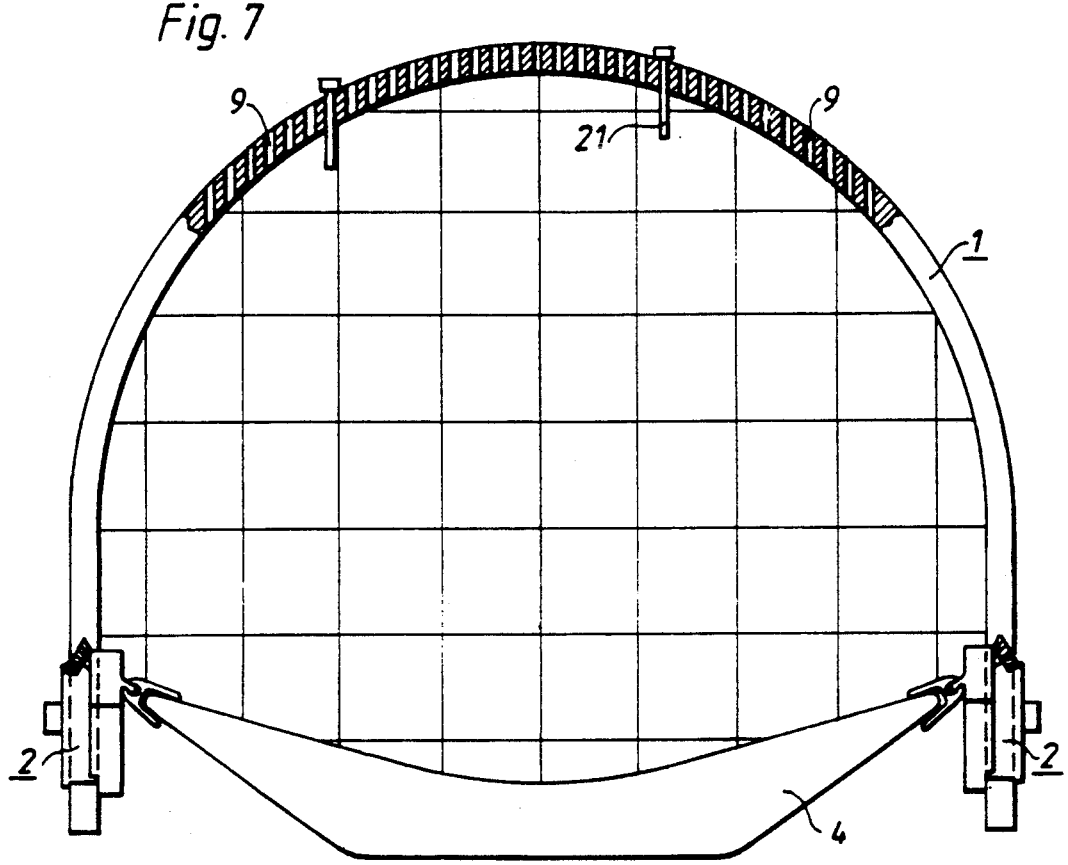
FIG. 7 shows a biopsy arc design with chordally directed apertures only.

In some connections it could be advisable to use arcs which e.g. have cordally directed apertures only. Such a structure is shown in FIG. 7.

Figure 8:
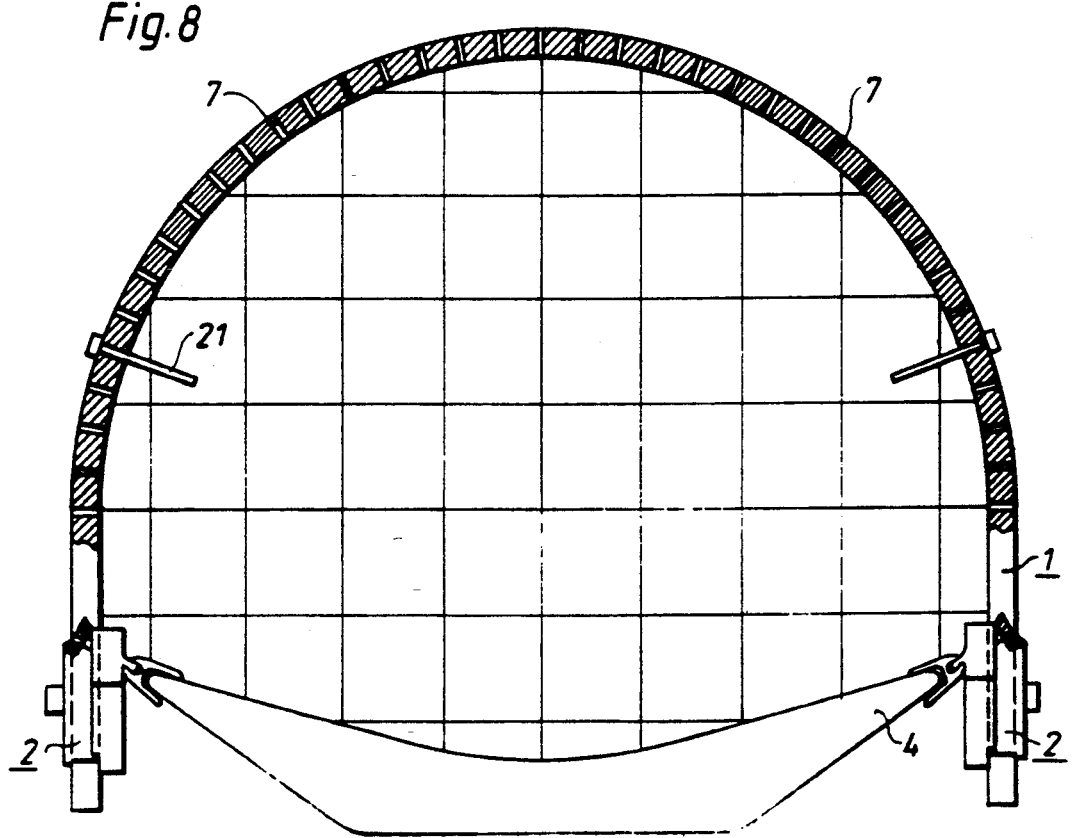
FIG. 8 shows a biopsy arc having radially directed apertures only.

Likewise it could be advisable sometimes to use an arc which has throughout radial apertures directed towards a central target point. Such a structure can be seen in FIG. 8.

As a matter of course a plurality of designs can be contemplated within the scope of the invention where, for instance, several different types of apertures 5 can occur. For example, such structures can be conceived wherein differently directed apertures are located adjacent one another or in the interspace between apertures.

Thus e.g. every second aperture can be radially directed, such as apertures 7, and every second chordally directed, as apertures 9. In a manner suitable for certain purposes groups of apertures can be distributed along the arc and have various directions. Of course also arrays of apertures adjacent each other can be provided, differently directed. Such solutions can be valuable if it is desirable to select an aperture having a very specific direction, in doing which the biopsy arc can be angularly tilted through the plane of the image section according to arrow 17 in order to determine the desired aperture.

The biopsy arc can also be secured to another base member than the patient's table shown. For example, a separate base slab can be used which can be placed on the patient's table and retained thereon by the patient resting on the slab by his own weight.

We claim:

1. A biopsy arc system for computed tomography comprising an arc which is adapted to be mounted archwise above a body that is to be examined, said arc being adjustably secured to a base member, the arc being provided with a plurality of apertures having axes which are directed towards the area within the arc, the arc being secured to the base member in such a way that it can be angularly adjusted in order to adapt a plane of the arc to an image section plane, the arc having a radiation attenuation coefficient which is essentially the same or smaller than a radiation attenuation coefficient exhibited by an organic tissue so that the arc will form a part of the associated image section plane whereby an axis of at least one of the apertures is identifiable in order that a suitable path may be selected for inserting an examination means through a selected aperture.

2. A biopsy arc system according to claim 1, wherein the apertures have a diameter larger than that of said examination means and wherein said arc includes a sleeve which is located in one of said apertures in the arc for receiving said examination means.

3. A biopsy arc system according to claim 1, wherein one group of the apertures has axes which are radially directed towards a point within the area bounded by the arc and a second group of apertures has axes with a chordal orientation within the arc, the arc being removably secured to a base member so that said arc, when loosened, can be turned and re-secured for adjustment to a proper aperture for an examination being performed.

4. A biopsy arc system according to claim 1, wherein said arc comprises shanks on each end of the arc which are clamped to slides running along side rails mounted on either side of the base member.

5. A biopsy arc system according to claim 4, wherein a plate is pivotally mounted on said slide and wherein said arc includes means for clamping the respective shank of the arc between the plate and the respective slide.

6. A biopsy arc system according to claim 1 wherein the arc is made of a material which has an attenuation coefficient with respect to X-ray radiation of 200 H or less.

7. A biopsy arc system according to claim 6, wherein the arc is made of polyamide plastic.

8. A biopsy arc system according to claim 1, wherein the arc is made of a material which has an attenuation coefficient with respect to X-ray radiation of 80 H or less.

9. A biopsy arc according to claim 1, wherein the arc is made of a material which has an attenuation coefficient with respect to X-ray radiation of 70 H or less.

10. A biopsy arc according to claim 1, wherein the arc is made of a material which has an attenuation coefficient with respect to X-ray radiation of 125 H or less.

11. A frame for use in computed tomography, comprising:
   an arc comprising a material having a radiation attenuation coefficient which is less than a radiation attenuation coefficient of some organic tissue that is to be examined;
   a plurality of apertures arranged in the arc having axes directed towards an area under the arc; and
   means for angularly adjusting the arc so that at least some of said aperture axes coincide with a section plane of a tomographic image in order to form a part of said tomographic image.

12. A frame according to claim 11, further comprising a sleeve arranged in one of said apertures for receiving a biopsy needle.

13. A frame according to claim 11 wherein the axes of some of said apertures are directed radially toward a center of said arc.

14. A frame according to claim 11 wherein the axes of some of said apertures are directed chordially on said arc.

15. A frame according to claim 11 wherein the axes of some of said apertures are directed radially toward a center of said arc and the axes of other of said apertures are directed chordially on said arc.

16. A frame according to claim 11 wherein said arc further comprises two shanks which are slideably connected to a base member.

17. A frame according to claim 11 wherein said attenuation coefficient with respect to X-ray radiation is less than or equal to 200 H.

18. A frame according to claim 11 wherein said attenuation coefficient with respect to X-ray radiation is less than or equal to 80 H.

19. A frame according to claim 11 wherein said arc material comprises any polyamide plastic.

20. A frame according to claim 11, wherein said attenuation coefficient with respect to X-ray radiation is less than or equal to 70 H.

21. A method of performing a biopsy, comprising the steps of:
   providing the biopsy arc of claim 1 making a tomographic image showing a plurality of radially directed apertures in a frame, said image also showing a reference point corresponding to an intersection of each of the axes of said apertures;
   selecting an appropriate aperture for guiding a biopsy needle by drawing a line from said reference point through a target point on said image to an appropriate one of said apertures;
   determining a depth of penetration for said biopsy needle according to a distance from said appropriate aperture to said target point; and
   penetrating said biopsy needle through said appropriate aperture to said target point.

22. A method of performing a biopsy, comprising the steps of:
   providing the frame for use in computed tomography of claim 10;
   making a tomographic image showing a plurality of apertures in a frame;
   selecting an appropriate aperture for guiding a biopsy needle by drawing a line along an axis of one of said apertures to a target point;
   determining a depth of penetration for said biopsy needle according to a distance from said appropriate aperture to said target point; and
   penetrating said biopsy needle through said appropriate aperture to said target point.

* * * * *